United States Patent [19]

Asanuma et al.

[11] Patent Number: 5,185,470
[45] Date of Patent: Feb. 9, 1993

[54] PROCESS FOR PRODUCING IRONE

[75] Inventors: Goro Asanuma, Kurashiki; Yoshin Tamai, Shibata, both of Japan

[73] Assignee: Kuraray Company, Ltd., Kurashiki, Japan

[21] Appl. No.: 831,344

[22] Filed: Feb. 5, 1992

[30] Foreign Application Priority Data

Feb. 19, 1991 [JP] Japan .................................. 3-46011

[51] Int. Cl.$^5$ .............................................. C07C 45/61
[52] U.S. Cl. ...................................... 568/341; 568/348
[58] Field of Search ................................ 568/341, 348

[56] References Cited

FOREIGN PATENT DOCUMENTS 61-57530  3/1986  Japan .................................. 568/341
2-258773 10/1990  Japan .................................. 568/341

OTHER PUBLICATIONS

Govrilyuk et al., J. Org. Chem. U.S.S.R, vol. 23, pp. 1877–1888 (1987).
Gebhard et al., Chem. Abst., vol. 112, #77608t (1990).
Gora et al., Chem. Abst., vol. 113, #59622j (1990).

*Primary Examiner*—James H. Reamer
*Attorney, Agent, or Firm*—Oblon, Spivak, McClelland, Maier & Neustadt

[57] ABSTRACT

Provided is a process which comprises conducting the ring-closure of pseudoirone in the presence of chlorosulfonic acid, which is inexpensive, to obtain in a high yield the α-cis form of irone, which has nearly the same fragrance as that of natural irones.

7 Claims, No Drawings

PROCESS FOR PRODUCING IRONE

BACKGROUND OF THE INVENTION

1. Field of the Invention

The present invention relates to a process for producing irones which have a violet-tone fragrance.

2 Description of the Related Art

Natural irones are contained in the essential oil of orrisroot in an amount of 60 to 80%, and said to be comprised of γ-irone (75%) and α-irone (25%).

Several processes have been reported for the synthesis of irones, and they all comprise, at their final step, conducting the ring-closure of pseudoirones.

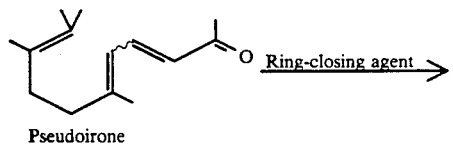

Pseudoirone

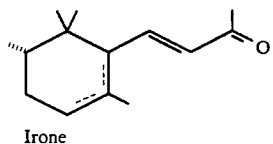

Irone

In the above reaction, there have been used as the ring closing agents Bronsted acids such as sulfuric acid and phosphoric acid and Lewis acids such as boron trifluoride and tin tetrachloride.

It is known that the ring closing of pseudirone gives a mixture of the following 3 types of irones.

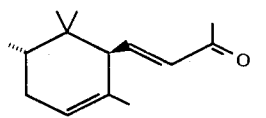

α-trans form

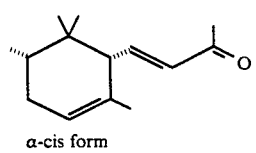

α-cis form

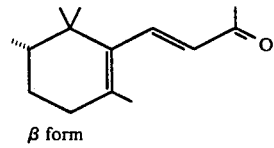

β form

Among the above, the α forms generate the fragrance of natural irones most representatively, while that of the β form is said to be more close to those of ionone and methylionone [Osamu Okuda, Koryo Kagaku Soran, Vol. 2, page 970 (Hirokawa publishing Co.)]. It is also said that, among the α forms, α-cis has better fragrance [Fragrance Journal, No. 17, page 72 (1976)].

It is also known that the ring closing of pseudoirone by the use of a mineral acid such as sulfuric acid or phosphoric acid gives the α-trans form preferentially to the α-cis, while the use of boron trifluoride or tin tetrachloride leads to formation of the α-cis form in preference to the α-trans. See, for example Chemical Abstract, 17833f (1957). Boron trifluoride and tin tetrachloride however are expensive and moreover, the use of tin tetrachloride raises the problem of waste water pollution. Thus, there has been established no process for the commercial production of the α-cis form in a high yield.

Japanese patent Application Laid-open No. 258773/1990 discloses a process for producing a cyclic terpene which comprises conducting ring-closing reaction in the presence of chlorosulfonic acid as a ring-closing agent. The cyclic terpene desired by this known reaction however contains no isomers, and hence the reaction is fundamentally different from the reaction for obtaining irone.

SUMMARY OF THE INVENTION

As a result of an extensive survey on ring-closing agents for producing the α-form in a high yield and that are inexpensive and usable from the viewpoint of commercial production, the present inventors have found that chlorosulfonic acid is effective for this purpose. Thus, the present invention provides a process for producing irone which comprises conducting the ring closure of pseudoirone in an organic solvent and in the presence of chlorosulfonic acid.

According to the process of the present invention, the α-cis form is obtained in nearly the same high yield as that of the α-trans form, the ratio varying to some extent depending on reaction conditions though. Since the total yield of the α-cis and -trans forms and β form by this process is high, a high yield of the β-form is realized. Chlorosulfonic acid used as a ring-closing agent in the present invention is inexpensive and does not cause the above-described problem of waste water pollution. The process of the present invention therefore can produce irone advantageously on an industrial scale.

DETAILED DESCRIPTION OF THE PREFERRED EMBODIMENT

The pseudoirone used in the process of the present invention can be obtained by condensing with acetone 6-methylcitral that is synthesized by reacting 2-methylprenol with senecialdehyde. The chlorosulfonic acid [$So_2Cl(OH)$] used in the present invention can be one that is commercially available, and is used in a molar ratio of 0.5 to 5.0 based on the mole of pseudoirone, more preferably in a molar ratio of 2.0 to 3.0 on the same basis. The reaction is preferably conducted at a temperature in a range of $-100°$ to $0°$ C., more preferably in a range of $-70°$ to $-30°$ C.

Any organic solvent that does not freeze at the above temperature can be used in the reaction of the present invention with no specific restriction, and its examples are hydrocarbons such as pentane, hexane and heptane; halohydrocarbons such as carbon tetrachloride, chloroform and methylene chloride; ketones such as acetone and methyl ethyl ketone; and nitroalkanes such as nitromethane and nitropropane. Methylene chloride is the most preferred among the above. The organic solvent is used in a ratio by volume of to 10 based on the volume of pseudoirone, preferably in a ratio by volume of about 5 on the same basis. The reaction time is 10 minutes to 1 hour.

The reaction of the present invention may be conducted by either batch or continuous system, but continuous system is preferred since longer contact time with chlorosulfonic acid will decrease the yield. The reaction process comprises dissolving pseudoirone in a solvent, cooling the solution to an appropriate temperature, and adding chlorosulfonic acid dropwise to the solution at such a rate that will not cause rapid temperature elevation. Since chlorosulfonic acid reacts vigorously with water, the reaction is preferably conducted under an atmosphere of nitrogen so that the reaction zone is protected from invasion of water. After the completion of the reaction, the reaction mixture is added to an aqueous alkaline solution such as aqueous sodium bicarbonate solution, the resulting mixture that formed is extracted with an organic solvent such as isopropyl ether, the extract is washed with an aqueous sodium chloride solution and the solvent is distilled off under reduced pressure. The crude product can be purified by distillation.

Other features of the invention will become apparent in the course of the following descriptions of exemplary embodiments which are given for illustration of the invention and are not intended to be limiting thereof.

EXAMPLES

Example 1 (Batch-type reaction)

A 300-ml three-necked flask equipped with a stirrer, a thermometer and a dropping funnel is charged with 20.6 g (0.10 mole) of pseudoirone and 140 ml of methylene chloride, and the flask was cooled in a dry ice-acetone bath to $-70°$ C. To the contents 20.6 g (0.177 mole) of chlorosulfonic acid was added dropwise over about 5 minutes while the inside temperature was maintained at $-65°$ to $-70°$ C. After the addition had been completed, the reaction mixture was further stirred for 5 minutes at the same temperature, and then, while being cooled, was emptied into about 300 ml of saturated aqueous sodium bicarbonate solution. The mixture was then subjected to extraction twice with 200 ml of isopropyl ether. The extract was washed with saturated aqueous sodium chloride solution twice and the solvent was distilled off with an evaporator, to obtain 12.5 g of irone. (Purity determined by gas chromatography: 97%, net weight: 12.13 g, yield: 58.9%).

Ratio of isomers: α-trans: 46.5%; α-cis: 41.5%; and 10.0%)

Conditions of gas chromatography

Column: silicone OV-1701, 0.25 mm-$\phi$×25 m.

Column temperature: 130° to 180° C., elevated at a rate of 2° C./min.

Example 2 (Continuous-type reaction)

A 100-ml three-necked flask equipped with a stirrer, a thermometer and a port for overflow liquid and having an effective volume of 60 ml was cooled in a dry ice-acetone bath to $-70°$ C. A solution of 41.2 g (0.20 mole) of pseudoirone in 140 ml of methylene chloride and that of 51.2 g (0.439 mole) of chlorosulfonic acid in 140 ml of methylene chloride were each added dropwise through a metering pump into the flask. The liquid overflown from the flask was treated in the same manner as in Example 1, to give 29.3 g of irone. (purity determined by gas chromatography: 98.5%, net weight: 28.80 9, yield: 70.4%).

Ratio of isomers: α-trans: 45.6%; α-cis: 43.3%; and β: 11.1%)

Comparative Example (Synthesis example of irone with 80% sulfuric acid)

A 100-ml three-necked flask equipped with a stirrer, a thermometer and a port for overflow liquid and having an effective volume of 60 ml was cooled in a dry ice-acetone bath to 0° to 5° C. A solution of 41.2 g (0.20 mole, 45.8 ml) of pseudoirone in 260 ml of methylene chloride and 90.5 g of an 80% by weight aqueous sulfuric acid solution (72.5 g as concentrated sulfuric acid, 0.74 mole) were added dropwise into the flask at a rate of 5.0 ml/min and 1.0 ml/min, respectively, each through a metering pump. The liquid overflown from the flask was treated in the same manner as in Example 1, to give 28.0 g of irone. (purity determined by gas chromatography: 96.5%, net weight: 27.0 g, yield: 65.5%)

Ratio of isomers: α-trans: 60.7%; α-cis: 12.4%; and β: 26.9%)

Obviously, numerous modifications and variations of the present invention are possible in light of the above teachings. It is therefore to be understood that within the scope of the appended claims, the invention may be practiced otherwise than as specifically described herein.

What is claimed is:

1. A process for producing irone, which comprises: conducting ring-closure of pseudoirone in the presence of chlorosulfonic acid in an organic solvent.

2. The process of claim 1, wherein the molar amount of chlorosulfonic acid relative to one mole of pseudoirone ranges from 0.5 to 5.0 mole.

3. The process of claim 1, wherein the ring-closure reaction is conducted at a temperature of $-100°$ to 0° C.

4. The process of claim 3, wherein said temperature ranges from $-70°$ to $-30°$ C.

5. The process of claim 2, wherein said amount of chlorosulfonic acid ranges from 2.0 to 3.0 moles.

6. The process of claim 1, wherein said organic solvent is a hydrocarbon, a halohydrocarbon, a ketone or a nitroalkane.

7. The process of claim 1, wherein the volume amount of organic solvent ranges from 1 to 10 based on a volume of pseudoirone.

* * * * *